(12) United States Patent
Romano et al.

(10) Patent No.: US 11,278,698 B2
(45) Date of Patent: Mar. 22, 2022

(54) BLENDING GAS ENRICHED PRESSURE SUPPORT SYSTEM AND METHOD

(71) Applicant: KONINKLIJKE PHILIPS N.V., Eindhoven (NL)

(72) Inventors: Robert Romano, Pittsburgh, PA (US); William Gaussa, Jeannette, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1120 days.

(21) Appl. No.: 15/122,951

(22) PCT Filed: Feb. 4, 2015

(86) PCT No.: PCT/IB2015/050835
§ 371 (c)(1),
(2) Date: Sep. 1, 2016

(87) PCT Pub. No.: WO2015/132682
PCT Pub. Date: Sep. 11, 2015

(65) Prior Publication Data
US 2017/0072159 A1    Mar. 16, 2017

Related U.S. Application Data

(60) Provisional application No. 61/947,460, filed on Mar. 4, 2014.

(51) Int. Cl.
*A61M 16/12* (2006.01)
*A61M 16/10* (2006.01)
*A61M 16/00* (2006.01)

(52) U.S. Cl.
CPC ...... *A61M 16/127* (2014.02); *A61M 16/0003* (2014.02); *A61M 16/0057* (2013.01);
(Continued)

(58) Field of Classification Search
CPC .......... A61M 16/0003; A61M 16/0057; A61M 16/101; A61M 16/127; A61M 2016/0015;
(Continued)

(56) References Cited

U.S. PATENT DOCUMENTS 3,368,555 A    2/1968  Beasley
3,726,274 A *  4/1973  Bird .................... A61M 16/201
                                          128/205.24

(Continued)

FOREIGN PATENT DOCUMENTS

JP    52071895 A    6/1977
JP     5434594 A    3/1979
(Continued)

*Primary Examiner* — Joseph D. Boecker
*Assistant Examiner* — Brian T Khong

(57) ABSTRACT

The present disclosure pertains to a system configured to amplify the pressure and/or flow rate of a pressurized flow of breathable gas by entraining oxygen gas and/or ambient air with an air amplifier and a venturi valve at or near a blending gas source, distally (e.g., remotely) from an interface appliance of a subject interface (e.g., away from the face of the subject) to reduce noise from the system heard by the subject. The system is configured to provide this pressure support and/or ventilation with oxygen therapy. The system is configured to deliver ventilatory and/or pressure support with oxygen therapy while decreasing output requirements of the blending gas source and/or pressure generator.

11 Claims, 6 Drawing Sheets

(52) U.S. Cl.
CPC ... *A61M 16/101* (2014.02); *A61M 2016/0015* (2013.01); *A61M 2016/0036* (2013.01); *A61M 2016/102* (2013.01); *A61M 2202/0208* (2013.01); *A61M 2205/17* (2013.01); *A61M 2205/3317* (2013.01); *A61M 2205/3334* (2013.01); *A61M 2205/3355* (2013.01); *A61M 2205/42* (2013.01); *A61M 2205/50* (2013.01); *A61M 2205/8206* (2013.01); *A61M 2230/40* (2013.01)

(58) Field of Classification Search
CPC .... A61M 2016/0036; A61M 2016/102; A61M 2202/0208; A61M 2205/17; A61M 2205/3317; A61M 2205/3334; A61M 2205/3355; A61M 2205/42; A61M 2205/50; A61M 2205/8206; A61M 2230/40
See application file for complete search history.

(56) References Cited

U.S. PATENT DOCUMENTS

| | | | | |
|---|---|---|---|---|
| 4,417,573 | A * | 11/1983 | De Vries | A61M 16/00 128/204.25 |
| 4,495,946 | A * | 1/1985 | Lerner | A61M 16/00 128/204.25 |
| 9,669,171 | B2 | 6/2017 | Ahmad | |
| 2002/0096174 | A1 * | 7/2002 | Hill | A61M 16/1075 128/205.11 |
| 2002/0104537 | A1 * | 8/2002 | Banner | A61M 16/0012 128/204.25 |
| 2005/0115566 | A1 * | 6/2005 | Van den Akker | A61M 16/00 128/205.24 |
| 2006/0113690 | A1 | 6/2006 | Huddart et al. | |
| 2006/0180149 | A1 * | 8/2006 | Matarasso | A61M 16/0069 128/204.18 |
| 2007/0056587 | A1 * | 3/2007 | Travan | A61M 16/127 128/204.18 |
| 2007/0107737 | A1 | 5/2007 | Landis et al. | |
| 2008/0135044 | A1 * | 6/2008 | Freitag | A61M 16/16 128/200.26 |
| 2010/0236551 | A1 * | 9/2010 | Enk | A61M 16/125 128/204.18 |
| 2011/0214676 | A1 * | 9/2011 | Allum | A61M 16/00 128/207.18 |
| 2013/0206144 | A1 | 8/2013 | Ahmad | |
| 2014/0020687 | A1 * | 1/2014 | Cullen | A61M 16/0816 128/204.23 |
| 2015/0107592 | A1 * | 4/2015 | Allum | A61M 16/024 128/204.21 |
| 2017/0182270 | A1 * | 6/2017 | Kenyon | A61M 16/0051 |

FOREIGN PATENT DOCUMENTS

| | | |
|---|---|---|
| JP | 54034594 A | 3/1979 |
| JP | 5271895 A | 6/1997 |
| WO | WO2006130369 A2 | 12/2006 |

* cited by examiner

BLENDING GAS ENRICHED PRESSURE SUPPORT SYSTEM AND METHOD

CROSS-REFERENCE TO RELATED APPLICATIONS

This patent application claims the priority benefit under 35 U.S.C. § 371 of international patent application no. PCT/IB2015/050835, filed Feb. 4, 2015, which claims the priority benefit under 35 U.S.C. § 119(e) of U.S. Provisional Application No. 61/947,460 filed on Mar. 4, 2014, the contents of which are herein incorporated by reference.

BACKGROUND

1. Field

The present disclosure pertains to a system configured to deliver a blending gas enriched pressurized flow of breathable gas to the airway of a subject.

2. Description of the Related Art

It is well known to apply a positive air pressure (PAP) to a patient's airway to keep the airway open and avoid collapse during breathing. This positive pressure effectively "splints" the airway, thereby maintaining an open passage to the lungs. Typical PAP systems include a ventilator, a respiratory circuit, a control unit, and a patient interface coupled with the patient's mouth or nose. Some of these systems entrain ambient air through the patient interface at the patient's mouth or nose, resulting in a loud jet noise at the patient. Typically, these systems are not compatible with oxygen concentrators.

SUMMARY

Accordingly, one or more aspects of the present disclosure relate to a system configured to deliver a blending gas enriched pressurized flow of breathable gas to the airway of a subject. The system comprises a pressure generator, a blending gas source, an air amplifier, a venturi valve, one or more sensors, one or more physical computer processors, and/or other components. The pressure generator is configured to generate compressed gas. The blending gas source is configured to provide blending gas. The air amplifier is configured to receive the compressed gas from the pressure generator and the blending gas from the blending gas source into the pressurized flow of breathable gas, and then amplify a pressure of the pressurized flow of breathable gas that includes the blending gas. The venturi valve is configured to receive the pressurized flow of breathable gas from the air amplifier and entrain ambient air into the pressurized flow of breathable gas during inhalation of the subject. The one or more sensors are configured to generate output signals conveying information related to one or more gas parameters of the pressurized flow of breathable gas. The one or more physical computer processors are configured by computer readable instructions to control the pressure generator, the blending gas source, and the air amplifier to deliver the pressurized flow of breathable gas to the subject according to a bi-level positive pressure support therapy regime based on the output signals.

Yet another aspect of the present disclosure relates to a method for delivering a blending gas enriched pressurized flow of breathable gas to the airway of a subject with a delivery system. The system comprises a pressure generator, a blending gas source, an air amplifier, a venturi valve, one or more sensors, one or more physical computer processors, and/or other components. The method comprises generating compressed gas with the pressure generator; providing blending gas with the blending gas source; receiving the compressed gas from the pressure generator with the air amplifier; receiving the blending gas from the blending gas source with the air amplifier, amplifying a pressure of the pressurized flow of breathable gas that includes the blending gas with the air amplifier; receiving, with the venturi valve, the pressurized flow of breathable gas from the air amplifier and entraining ambient air into the pressurized flow of breathable gas during inhalation of the subject; generating, with the one or more sensors, output signals conveying information related to one or more gas parameters of the pressurized flow of breathable gas; and controlling, with the one or more physical computer processors, the pressure generator, the blending gas source, and the air amplifier to deliver the pressurized flow of breathable gas to the subject according to a bi-level positive pressure support therapy regime based on the output signals.

Still another aspect of the present disclosure relates to a system configured to deliver a blending gas enriched pressurized flow of breathable gas to the airway of a subject. The system comprises means for generating compressed gas; means for providing blending gas; means for receiving the compressed gas from the means for generating and the blending gas from the means for providing, and amplifying a pressure of the pressurized flow of breathable gas that includes the blending gas; means for receiving the pressurized flow of breathable gas from the means for receiving and amplifying, and entraining ambient air into the pressurized flow of breathable gas during inhalation of the subject; means for generating output signals conveying information related to one or more gas parameters of the pressurized flow of breathable gas; and means for controlling the means for generating, the means for providing, and the means for receiving and amplifying to deliver the pressurized flow of breathable gas to the subject according to a bi-level positive pressure support therapy regime based on the output signals.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1A:
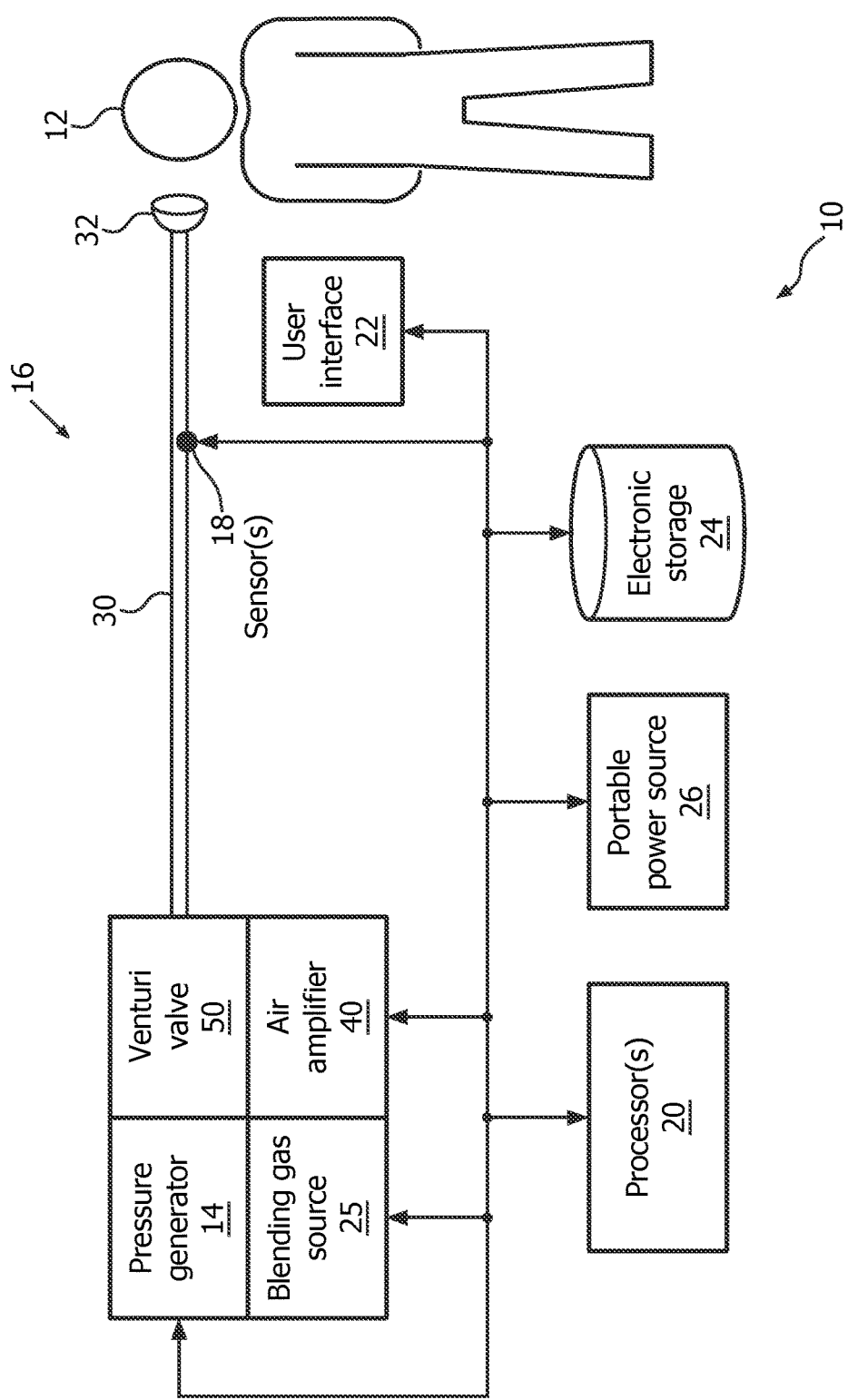
FIG. 1A is a schematic of a blending gas enriched pressure support system.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1A schematically illustrates a blending gas enriched pressure support system 10. System 10 is configured to deliver a blending gas enriched pressurized flow of breathable gas to the airway of a subject 12. In some embodiments, system 10 includes one or more of a pressure generator 14, a blending gas source 25, an air amplifier 40, a venturi valve 50, a subject interface 16, a sensor 18, a processor 20, a user interface 22, electronic storage 24, a portable power source 26, and/or other components.

Patients with chronic respiratory insufficiency frequently experience shortness of breath, referred to as dyspnea, and a decrease in blood oxygen saturation, a condition known as oxygen desaturation. These conditions result in a reduced capacity for exertion and exercise tolerance. To overcome these problems a patient often requires long term oxygen treatment (LTOT) to maintain blood oxygen levels and/or positive pressure support/ventilation to unload the respiratory muscles and reduce the work of breathing. System 10 overcomes problems delivering these therapies portably through a convenient, portable, light-weight, compact device configured to deliver oxygen (and/or other blending gases) during bi-level pressure support, and/or other therapy. System 10 may be used during and/or after pulmonary rehabilitation with the goal of allowing the patients to achieve a higher maximal exercise capacity (MEC), for example. System 10, due to its lightweight design, may be used to increase patient mobility during daily ambulatory activities, thereby increasing quality of life. System 10 may be used nocturnally to treat patients with obstructive sleep apnea, and/or chronic obstructive pulmonary disease (COPD). For patients with COPD, respiratory insufficiency evolves into a decrease in activity, skeletal muscle atrophy, depression and ultimately systemic cardio-pulmonary failure. System 10 may slow this progressive downward spiral by improving a patient's quality of life by allowing them to have increased mobility with improved respiratory and skeleton muscle strength.

System 10 is configured to amplify the pressure and/or flow rate of a pressurized flow of breathable gas with air amplifier 40, venturi valve 50, and/or other components of system 10. System 10 is configured to entrain and/or add ambient air to augment a flow of oxygen and/or other blending gasses using air amplifier 40, venturi valve 50, and/or other components for air entrainment. Air amplifier 40 and/or venturi valve 50 are configured to entrain blending gas (e.g., oxygen) and/or ambient air to form and/or compliment the pressurized flow of breathable gas at or near blending gas source 25, distally (e.g., remotely) from an interface appliance 32 of subject interface 16 (e.g., away from the face of subject 12) to reduce noise from system 10 heard by subject 12. System 10 is configured to provide pressure support and/or ventilation with oxygen (for example) therapy. System 10 is configured to deliver ventilatory and/or pressure support while decreasing output requirements (e.g., blending gas pressure, blending gas flow rate) of blending gas source 25 and/or pressure generator 14. No known systems use the combination of components of system 10 in the way described in this disclosure (e.g., using an air amplifier/venturi valve to generate therapeutic flow rates/pressures) to decrease the output requirements of a blending gas source and/or a pressure generator. No known pressure support systems describe using an air amplifier and a venturi valve at or near the blending gas source, distally from the subject interface, to provide pressure support/ ventilation with decreased noise.

Figure 1B:
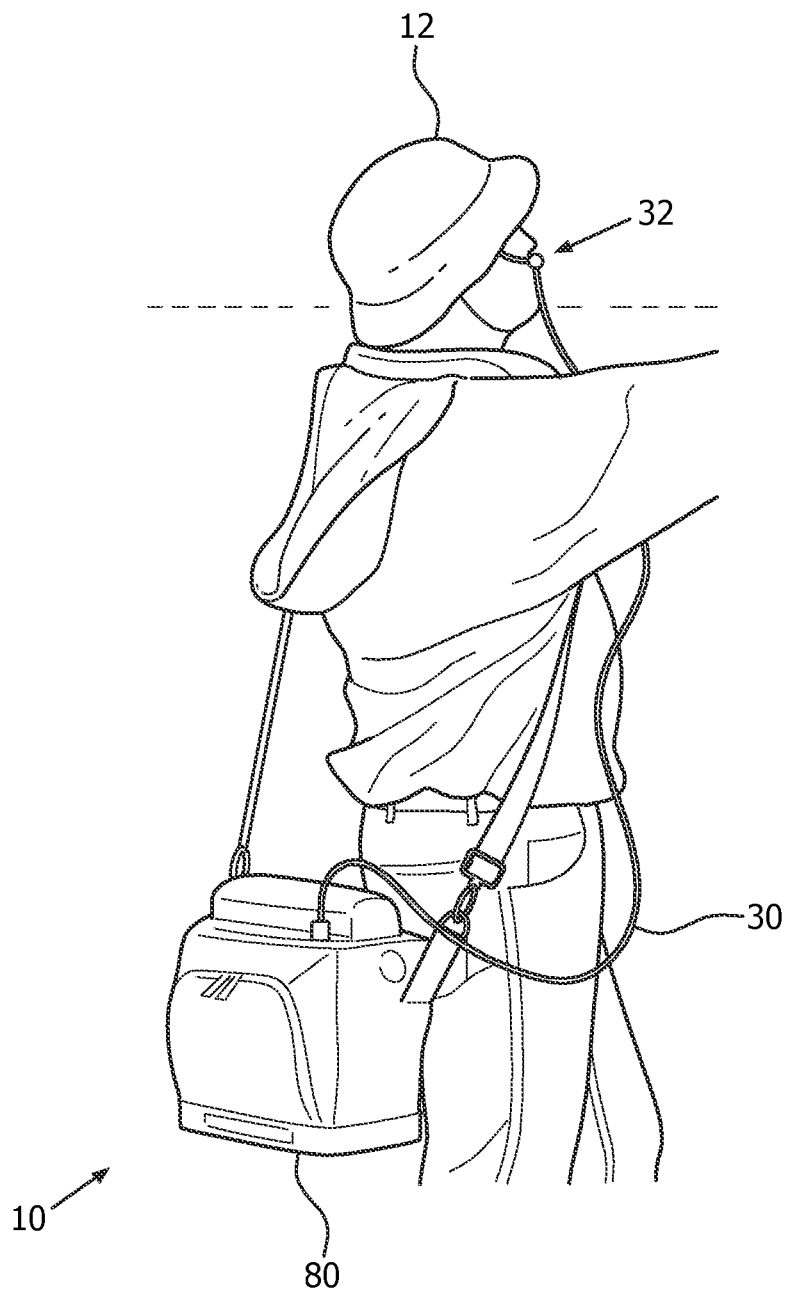
FIG. 1B illustrates a subject using the blending gas enriched pressure support system.

By way of a non-limiting example, FIG. 1B illustrates subject 12 using blending gas enriched pressure support system 10. In FIG. 1B, pressure generator 14, blending gas source 25, air amplifier 40, venturi valve 50, processor 20, user interface 22, electronic storage 24, portable power source 26, and/or other components of system 10 are located inside portable bag 80. Pressure generator 14, blending gas source 25, air amplifier 40, and venturi valve 50 are coupled with interface appliance 32 via conduit 30. Pressure generator 14, blending gas source 25, air amplifier 40, and venturi valve 50 are located remotely from interface appliance 32 to reduce noise from pressure generator 14, blending gas source 25, air amplifier 40, and/or venturi valve 50 heard by subject 12.

Figure 2:
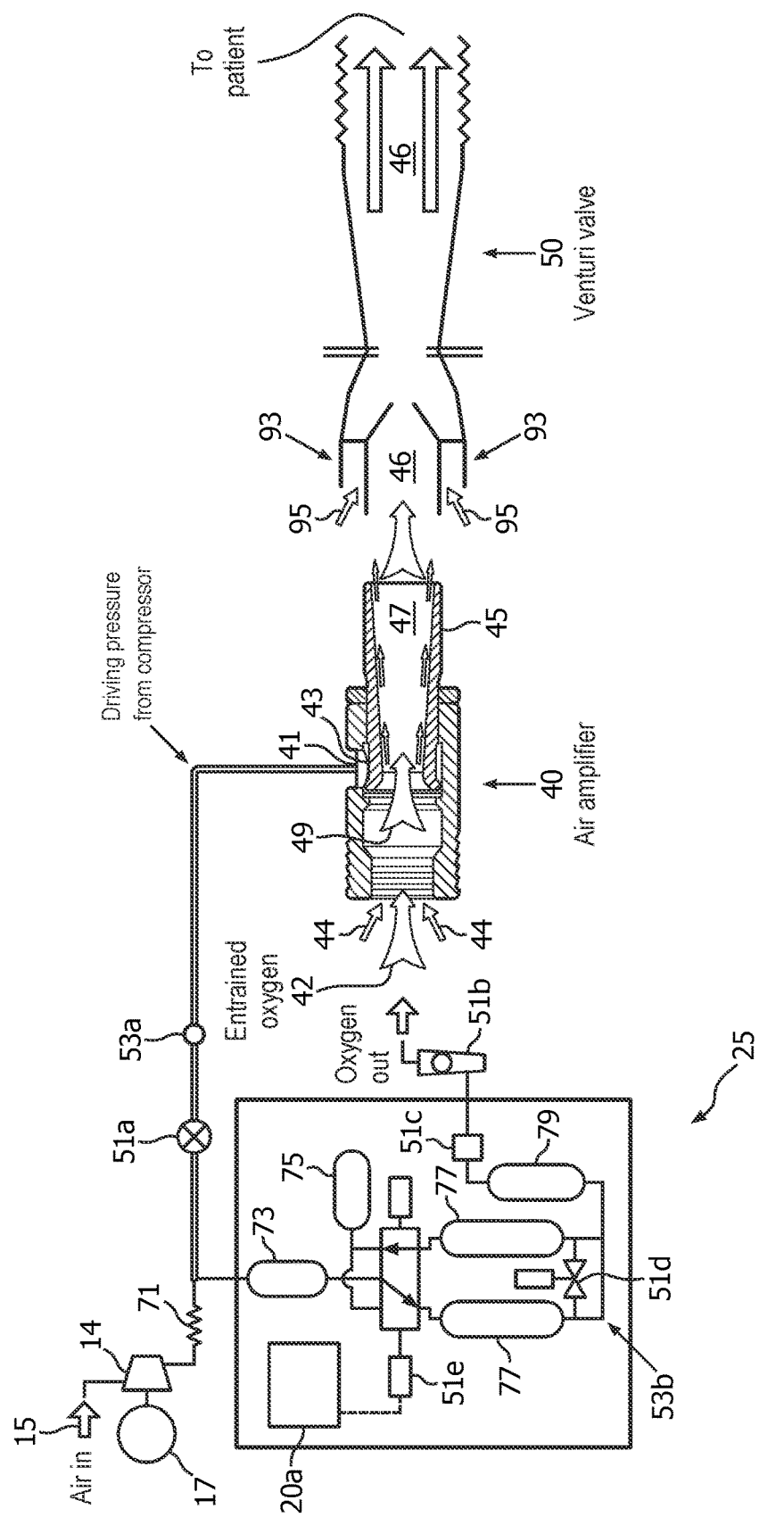
FIG. 2 illustrates the flow of gas during an inspiratory respiration phase.
Figure 3:
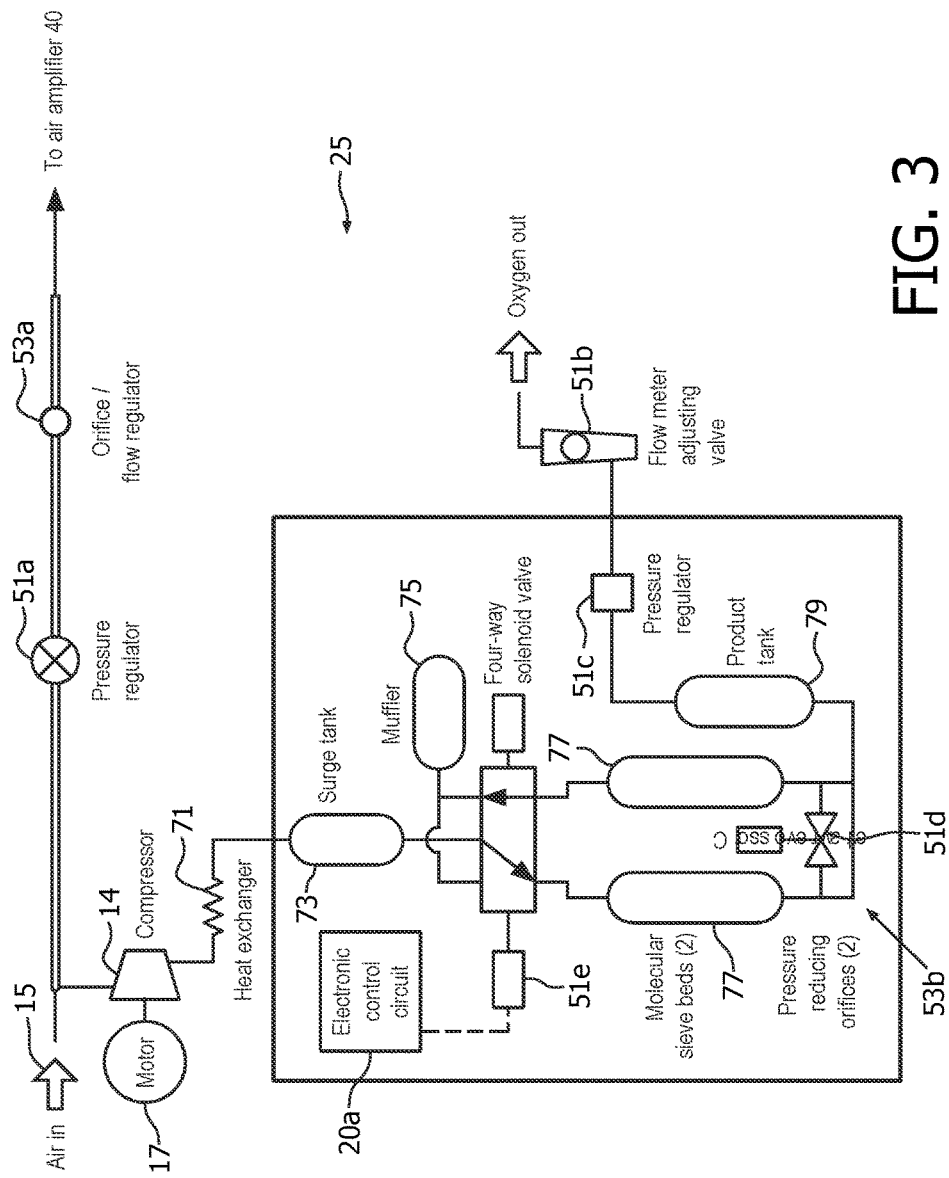
FIG. 3 illustrates an example of a blending gas source.
Figure 4:
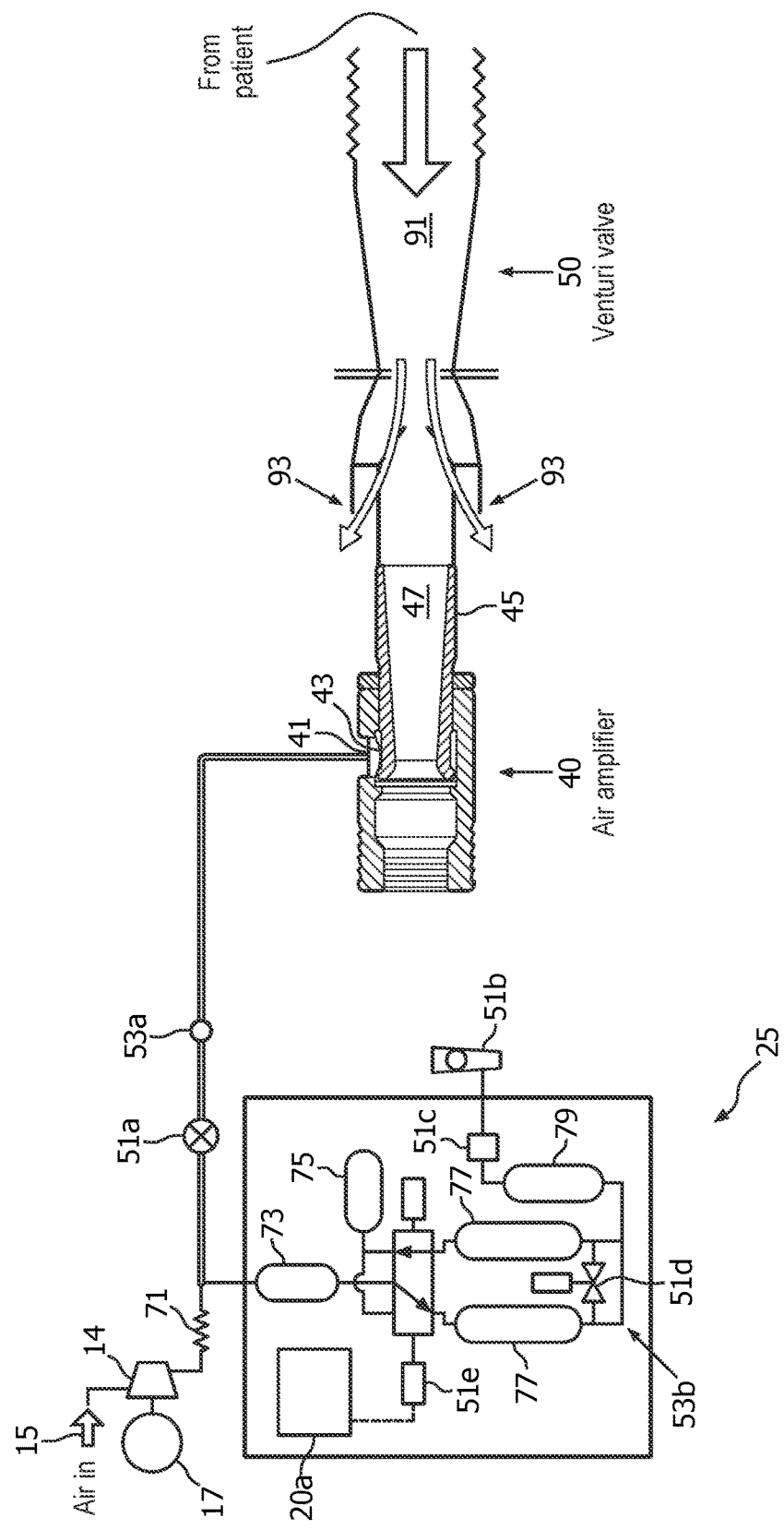
FIG. 4 illustrates the flow of gas during an expiratory respiration phase.

FIGS. 2-4 illustrate pressure generator 14, blending gas source 25, air amplifier 40, and venturi valve 50 in more detail. For example, FIG. 2 illustrates a flow of gas during an inspiratory phase of subject 12. Pressure generator 14 is configured to provide compressed gas for delivery to air amplifier 40 and/or blending gas source 25. In some embodiments, blending gas source 25 may receive compressed gas from sources in addition to, and/or other than pressure generator 14. In some embodiments, air amplifier may receive compressed gas from sources in addition to and/or other than pressure generator 14.

Pressure generator 14 may control one or more parameters of the compressed gas, thereby impacting one or more parameters of the flow of pressurized gas delivered to subject 12 (e.g., flow rate, pressure, volume, etc.) for therapeutic purposes, and/or for other purposes. Pressure generator 14 receives a flow of gas from a gas source 15, such as the ambient atmosphere, and compresses (e.g., elevates the pressure of) that gas for delivery to air amplifier 40 and/or blending gas source 25. Pressure generator 14 is any device, such as, for example, a pump, blower, piston, or bellows, that is capable of elevating the pressure of the received gas for delivery to air amplifier 40 and/or blending gas source 25. Pressure generator 14 may include a motor 17. Pressure generator 14 may comprise one or more valves for controlling the pressure/flow of gas. The present disclosure also contemplates controlling the operating speed of the blower, either alone or in combination with such valves, to individually control the pressure/flow of gas provided to air amplifier 40 and/or blending gas source 25. In some implementations, pressure generator 14 may be associated with and/or included in blending gas source 25.

Blending gas source 25 is configured to provide blending gas. In some embodiments, blending gas source 25 is configured such that the blending gas is oxygen. In these embodiments, blending gas source 25 may be an oxygen concentrator (shown in FIG. 2, FIG. 3, and FIG. 4), bottled compressed oxygen, liquid oxygen, and/or other oxygen sources. In some embodiments, blending gas source 25 is and/or includes a pressure swing adsorption oxygen concentrator. In some embodiments, blending gas source is and/or includes an oxygen gas source that is a small compressed oxygen gas cylinder that provides oxygen to system 10 and provides a driving pressure to run air amplifier 40. In some embodiments, blending gas source is and/or includes an oxygen source comprising liquefied oxygen cylinder that provides oxygen to system 10 and provides a driving pressure to run air amplifier 40.

Blending gas source 25 may be controlled by processor 20 (described below) such that a timing for providing oxygen gas will correspond to the respiratory cycle of subject 12 and will be controlled based on an intelligent oxygen delivery algorithm similar to and/or the same as those described in U.S. patent application Ser. No. 13/131,622 filed Nov. 21, 2009, and entitled, "Variable Flow Oxygen Therapy", which is hereby incorporated by reference in its entirety. As described herein, the blending (e.g., oxygen) gas may be augmented by filtered and/or compressed ambient air that is generated by pressure generator 14, ambient air entrained by air amplifier 40 and/or venturi valve 50, and/or other gas to form the pressurized flow of breathable gas. The pressure and/or flow rate of the pressurized flow of breathable gas that includes the blending gas may be increased by air amplifier 40 and/or venturi valve 50, for example. It should be noted that the description of oxygen as the blending gas is not intended to be limiting. The blending gas may be any gas and/or combination of gases that allows system 10 to function as described herein.

FIG. 3 illustrates an example of blending gas source 25 in more detail relative to FIG. 2. In FIG. 3, blending gas source 25 is illustrated as an oxygen concentrator. The oxygen concentrator may receive gas from compressor 14 via a heat exchanger 71. The oxygen concentrator may include one or more of a surge tank 73, a muffler 75, an electrical control circuit 20a (e.g., one or more processors 20), a four-way solenoid valve 51e, molecular sieve beds 77, pressure reducing orifices 53b, a cross over valve 51d, a product tank 79, a pressure regulator 51c, a flow meter adjusting valve 51b, and/or other components.

Returning to FIG. 2, air amplifier 40 is configured to receive the compressed gas from pressure generator 14, the blending gas from blending gas source 25, and/or other gas (e.g., ambient air). Air amplifier 40 is configured to blend the blending gas into the pressurized flow of breathable gas and amplify a pressure of the pressurized flow of breathable gas that includes the blending gas. Air amplifier 40 may be configured such that the compressed gas from pressure generator 14 flows through an inlet 41 into an annular chamber 43. The compressed gas is throttled through a small ring nozzle (not shown). The throttled airstream then adheres to the profile of the coanda nozzle 45 and flows toward an outlet 47 of air amplifier 40. This creates an area of low pressure 49 on the interior of air amplifier 40 which draws in blending gas (oxygen 42 for example) from blending gas source 25 and ambient air 44 to form the pressurized flow of breathable gas 46. In some embodiments, air amplifier 40 receives the compressed gas from pressure generator 14 and the blending gas from blending gas source 25, but does not draw in additional ambient air. In some embodiments, ambient air 44 entrained by air amplifier 40 is included in the blending gas from blending gas source 25 (e.g., purified oxygen may have a purity level of about 90%.)

Venturi valve 50 is configured to receive the pressurized flow of breathable gas from the air amplifier and entrain ambient air 95 into the pressurized flow of breathable gas during inhalation of subject 12 (shown in FIG. 1, FIG. 2). Venturi valve 50 is configured to increase the volume of gas delivered to subject 12 during inhalation. System 10 is configured such that the pressurized flow of breathable gas is conveyed from venturi valve 50 to the airway of subject 12 via subject interface 16. System 10 may include one or more optional valves 51a-51e and/or orifices 53a-53b to regulate the flow rate and/or pressure of the pressurized flow of breathable gas delivered in the inspiratory phase, and/or the expiratory phase of subject 12. For example, system 10 may include one or more components that are similar to and/or the same as one or more components of the systems described in U.S. patent application Ser. No. 13/141,782 filed Dec. 9, 2009, and entitled, "System And Respiration Appliance For Supporting The Airway Of A Subject," and/or U.S. patent application Ser. No. 13/141,777 filed Dec. 9, 2009, and entitled, "System And Respiration Appliance For Supporting The Airway Of A Subject," both of which are hereby incorporated by reference in their entirety.

FIG. 4 illustrates the flow of gas during an expiratory phase of subject 12 (shown in FIG. 1, FIG. 2). Coanda nozzle 45 of air amplifier 40 may be charged with blending gas from blending gas source 25 during expiration of subject 12. Venturi valve 50 may be configured such that exhaled gas 91 from subject 12 is released to the ambient atmosphere through one or more ports 93 in venturi valve 50.

Returning to FIG. 1, subject interface 16 is configured to communicate the pressurized flow of breathable gas to the airway of subject 12. In some embodiments, subject interface 16 is configured to communicate the pressurized flow of breathable gas from venturi valve 50 to the airway of subject 12. As such, subject interface 16 comprises one or more of a conduit 30, an interface appliance 32, and/or other components.

Interface appliance 32 is configured to deliver the flow of gas to the airway of subject 12. In some embodiments, interface appliance 32 is configured to be non-invasively engaged by the nose and/or mouth of subject 12. Non-invasive engagement comprises removably engaging one or more external orifices of the airway of subject 12 (e.g., nostrils and/or mouth) to communicate gas between the airway of subject 12 and interface appliance 32. In some embodiments, interface appliance 32 is removably coupled to conduit 30. Interface appliance 32 may be removed for cleaning and/or for other purposes. Some examples of non-invasive interface appliance 32 may comprise, for example, a nasal cannula, a nasal mask, a nasal/oral mask, a full face mask, a total face mask, and/or other interface appliances that communicate a flow of gas with an airway of a subject. In some embodiments, interface appliance 32 is invasive. Some examples of invasive interface appliances that may comprise interface appliance 32 are endotracheal tubes, tracheostomy tubes, and or other devices. The present disclosure is not limited to these non-invasive and/or invasive examples, and contemplates delivery of the flow of gas to the subject using any interface appliance.

Subject interface 16 may further comprise optional valves and/or orifices that serve to regulate an amount of inspiratory pressure, an inspiratory flow rate, an expiratory pressure, an expiratory flow rate, and/or other parameters of the pressurized flow of breathable gas that is delivered to the airway of subject 12. In some embodiments, the inspiratory pressure, the expiratory pressure, or both, may be regulated by encapsulated valves and/or orifices. For example, if subject 12 requires greater flow than system 10 is able to deliver, then the use of one-way inspiration valves will allow the subject 12 to freely inhale additional ambient air. As another example, in the case of a patient that requires expiratory resistance to counter their intrinsic positive end expiratory pressure (PEEP), then the use of fixed and/or regulated expiratory orifices may provide additional positive expiratory pressure (PEP). PEP may also be provided by system 10 delivering an appropriate level of gas during the patient's expiratory phase.

Although subject interface 16 is illustrated in FIG. 1 as a single-limbed interface for the delivery of the flow of gas to the airway of the subject, this is not intended to be limiting. The scope of this disclosure also includes double-limbed circuits having a first limb configured to both provide the flow of gas to the airway of the subject, and a second limb configured to selectively exhaust gas (e.g., to exhaust exhaled gases). The single and/or dual limbs (e.g., conduits 30) may be small diameter, flexible gas delivery circuits configured not only for the transport of gases but to communicate indications of the spontaneous respiration of subject 12 in order to trigger a flow of gas (described below). Conduits 30 are configured to convey the pressurized flow of gas to interface appliance 32. Conduits 30 may be a flexible length of hose, and/or other conduits, that place interface appliance 32 in fluid communication with other components of system 10 (e.g., venturi valve 50, air amplifier 40, pressure generator 14). In some implementations, conduits 30 may be flexible tubing having a diameter less than about 22 mm. In some implementations, conduits 30 will be of sufficient diameter to effectively deliver the pressurized flow of breathable gas with a flow rate and/or pressure that maintains adequate pressure support ventilation.

In some implementations, subject interface 16 may include a dual lumen type conduit 30 where a small bore lumen is used to sense (e.g., see the descriptions of sensor 18 and processor 20 below) the respiration pattern of subject 12 and control the pressurized flow of breathable gas in synchrony with the spontaneous breathing of the subject.

Sensor 18 is configured to generate output signals conveying information related to one or more gas parameters of the pressurized flow of breathable gas within system 10. The one or more parameters of the gas within system 10 may comprise gas parameters related to the pressurized flow of breathable gas, breathing parameters related to respiration of subject 12, blending gas parameters related to the flow of blending gas from blending gas source 25, and/or other parameters. Sensor 18 may comprise one or more sensors that measure such parameters directly (e.g., through fluid communication with the flow of gas in interface appliance 32 and/or conduit 30). Sensor 18 may comprise one or more sensors that generate output signals related to the one or more parameters indirectly. For example, sensor 18 may comprise one or more sensors configured to generate an output based on an operating parameter of pressure generator 14 (e.g., motor current, voltage, rotational velocity, and/or other operating parameters), and/or other sensors.

The one or more gas parameters of the pressurized flow of breathable gas may comprise, for example, one or more of a flow rate, a volume, a pressure, humidity, temperature, acceleration, velocity, concentration of one or more constituents (e.g., the concentration of oxygen), and/or other gas parameters. Breathing parameters related to the respiration of subject 12 may comprise a tidal volume, a timing (e.g., beginning and/or end of inhalation, beginning and/or end of exhalation, etc.), a respiration rate, a duration (e.g., of inhalation, of exhalation, of a single breathing cycle, etc.), respiration frequency, and/or other breathing parameters. Blending gas parameters related to the flow of blending gas from blending gas source 25 may comprise, for example, a blending gas pressure, a blending gas flow rate, a blending gas composition, and/or other blending gas parameters.

In some embodiments, sensor 18 comprises one or more flow rate sensors configured to generate output signals conveying information related to the flow rate of the pressurized flow of breathable gas, the flow rate of the compressed gas from pressure generator 14, and/or the flow rate of the blending gas from blending gas blending gas source 25. Flow rate sensors suitable for use as sensor 18 may include, for example, mechanical flow rate sensors, pressure based flow rate sensors, optical flow rate sensors, thermal mass flow rate sensors, magnetic flow rate sensors, and/or other flow rate sensors.

In some embodiments, sensor 18 comprises one or more pressure sensors configured to generate output signals conveying information related to the pressure of the pressurized flow of breathable gas, the compressed gas generated by pressure generator 14, and/or the pressure of the blending gas flowing from blending gas source 25. Pressure sensors suitable for use as sensor 18 may include, for example, mechanical sensors, capacitive sensors, electromagnetic sensors, piezoelectric sensors, optical sensors, dual lumen sensors, and/or other pressure sensors.

In some embodiments, sensor 18 may comprise one or more oxygen sensors configured to generate output signals related to the concentration of oxygen in the pressurized flow of breathable gas delivered to subject 12.

Although sensor 18 is illustrated in FIG. 1 at a single location in system 10, this is not intended to be limiting. Sensor 18 may comprise sensors disposed in a plurality of locations, such as for example, at various locations within (or in communication with) conduit 30, within pressure generator 14, within (or in communication with) interface appliance 32, within (or in communication with) blending gas source 25, within (or in communication with) air amplifier 40, within (or in communication with) venturi valve 50, and/or other locations.

Processor 20 is configured to provide information processing capabilities in system 10. As such, processor 20 may comprise one or more of a digital processor, an analog processor, a digital circuit designed to process information, an analog circuit designed to process information, a state machine, and/or other mechanisms for electronically processing information. Although processor 20 is shown in FIG. 1 as a single entity, this is for illustrative purposes only. In some implementations, processor 20 may comprise a plurality of processing units. These processing units may be physically located within the same device (e.g., pressure generator 14), or processor 20 may represent processing functionality of a plurality of devices operating in coordination.

Processor 20 is configured, by computer readable instructions, to control pressure generator 14, blending gas source 25, air amplifier 40, and/or other components of system 10 to deliver the pressurized flow of breathable gas to the subject according to a ventilation and/or positive pressure support therapy regime. Ventilation and/or positive airway pressure support therapy may be used to maintain an open airway in subject 12 so that oxygen, carbon dioxide, and/or other gases may be exchanged more easily, requiring little and/or no effort from subject 12. Processor 20 may be configured to control the system components based on the output signals from sensor 18 and/or other information.

By way of non-limiting example, processor 20 may control the components of system 10 such that the pressure support provided to subject 12 via the pressurized flow of breathable gas comprises continuous positive airway pressure support (CPAP), bi-level positive airway pressure support (BPAP), proportional positive airway pressure support (PPAP), a ventilation therapy regime, non-classical waveform therapies, and/or other types of pressure support therapy.

CPAP supplies a fixed positive pressure to maintain a continuous level of positive airway pressure in a patient. BPAP provides a first inspiratory pressure (IPAP) and a second, typically lower, expiratory pressure (EPAP) for easier exhalation during ventilation. In some therapy modes (e.g., PPAP), system 10 may apply variable pressure support in which the amount of pressure delivered to the patient during inhalation and/or during exhalation is determined and delivered on a breath by breath basis.

For example, processor 20 is configured such that controlling pressure generator 14, blending gas source 25, air amplifier 40, and/or other components of system 10 to deliver the pressurized flow of breathable gas to subject 12 according to a positive pressure support therapy regime may include determining inhalation phases and/or exhalation phases during breathing of subject 12 based on the output signals and/or other information; controlling pressure generator 14 to adjust a positive end expiratory pressure (PEEP) in subject 12 based on the output signals, the inhalation and/or exhalation phase determinations, the positive pressure support therapy regime settings, and/or other information; controlling blending gas source 25 to adjust an amount and/or timing of blending gas in the pressurized flow of breathable gas based on the output signals, the inhalation and/or exhalation phase determinations, the positive pressure support therapy regime settings, an intelligent oxygen delivery algorithm, and/or other information. System 10 may be configured such that the pressurized flow of gas is delivered with an inspiratory pressure greater than the expiratory pressure so as to elevate the lung volume and/or airway pressure of subject 12 above spontaneous breathing levels in order to increase alveolar ventilation and/or unload the work of breathing. Controlling pressure generator 14, blending gas source 25, air amplifier 40, and/or other components of system 10 may include controlling one or more valves associated with pressure generator 14, blending gas source 25, and/or air amplifier 40.

As described above, in some embodiments, processor 20 is configured to control pressure generator 14, blending gas source 25, air amplifier 40, and/or other components of system 10 such that the blending gas (e.g., oxygen) is delivered using intelligent variable flow oxygen therapy algorithms. Blending gas delivery may be controlled such that it corresponds to respiratory cycle detections, and/or other information. The respiratory cycles may include an inspiratory phase and an expiratory phase. This intelligent delivery of the gas mixture may conserve the use of the blending gas, maximize the effectiveness of the blending gas on the pulmonary system of subject 12, and/or have other effects. In some embodiments, the variable flow delivery method of blending gas therapy may include a blending gas delivery rate that varies in accordance with the patient's rate of breathing.

In some embodiments, processor 20 is configured to control pressure generator 14, blending gas source 25, air amplifier 40, and/or other components of system 10 in accordance with a blending gas delivery algorithm such that subject interface 16 is charged with blending gas from the blending gas source during expiration of subject 12. This may purge expired $CO_2$ from the system, preventing $CO_2$ re-breathing, for example. On inspiration, a fresh dose of blending gas may be delivered where and when it is needed most by subject 12. The oxygen flow during expiration may also augment the end expiratory pressure (EPAP) profile.

User interface 22 is configured to provide an interface between system 10 and subject 12 and/or other users through which subject 12 and/or other users may provide information to and receive information from system 10. Other users may comprise, for example, a caregiver, a doctor, and/or other users. This enables data, cues, results, and/or instructions and any other communicable items, collectively referred to as "information," to be communicated between a user (e.g., subject 12) and one or more of pressure generator 14, processor 20, and/or other components of system 10. For example, a user may specify one or more therapy regimes and/or therapy regime set points that are to be delivered to subject 12 using user interface 22. As another example, a user may specify a blending gas dosage to be delivered to subject 12. As a third example, therapy pressures, the breath rate of subject 12, a portable power source energy level, and/or other information may be displayed to a user (e.g., subject 12) via user interface 22.

Examples of interface devices suitable for inclusion in user interface 22 comprise a keypad, buttons, switches, a keyboard, knobs, levers, a display screen, a touch screen, speakers, a microphone, an indicator light, an audible alarm, a printer, a tactile feedback device, and/or other interface devices. In one embodiment, user interface 22 comprises a plurality of separate interfaces. In one embodiment, user interface 22 comprises at least one interface that is provided integrally with pressure generator 14, blending gas source 25, air amplifier 40, venturi valve 50, and/or processor 20.

It is to be understood that other communication techniques, either hard-wired or wireless, are also contemplated by the present disclosure as user interface 22. For example, the present disclosure contemplates that user interface 22 may be integrated with a removable storage interface provided by electronic storage 24. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 22 comprise, but are not limited to, an RS-232 port, RF link, an IR link, modem (telephone, cable or other). In short, any technique for communicating information with system 10 is contemplated by the present disclosure as user interface 22.

In some embodiments, electronic storage 24 comprises electronic storage media that electronically stores information. The electronic storage media of electronic storage 24 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 24 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), and/or other electronically readable storage media. Electronic storage 24 may store software algorithms (e.g., intelligent variable flow oxygen therapy algorithms), information determined by processor 20, information received via user interface 22, and/or other information that enables system 10 to function as described herein. Electronic storage 24 may be (in whole or in part) a separate component within system 10, or electronic storage 24 may be provided (in whole or in part) integrally with one or more other components of system 10 (e.g., user interface 22, processor 20, etc.).

Information determined by processor 20 and/or stored by electronic storage 24 may comprise information related to respiration of subject 12, an amount of blending gas, therapy settings, and/or other information. The information stored by electronic storage 24 may be viewed via user interface 22, by connecting (wired and/or wireless) to a separate computer, and/or other via other methods. The information stored by electronic storage 24 may be used, for example, to adjust therapy settings, to make adjustments to power source 26, used by a doctor to make medical decisions, and/or for other uses.

In some embodiments, system includes portable power source 26. Portable power source 26 is configured to power pressure generator 14; blending gas source 25; sensor 18; processor 20; user interface 22; electronic storage 24; one or more valves 51a-51e associated with pressure generator 14, blending gas source 25, and/or air amplifier 40; and/or other components of system 10 in a portable manner. Power source 26 may comprise one or more power sources connected in series and/or in parallel. In some embodiments, power source 26 is rechargeable. Power source 26 may be recharged via a home AC power source, a car battery outlet, an airplane power outlet, a USB port, a non-contact charging circuit, and/or other recharging methods. Examples of portable power sources that may be included as portable power source 26 include one or more DC batteries, lithium ion cells, lithium polymer cells, nickel metal hydride, a solar power system, and/or other portable power sources.

Figure 5:
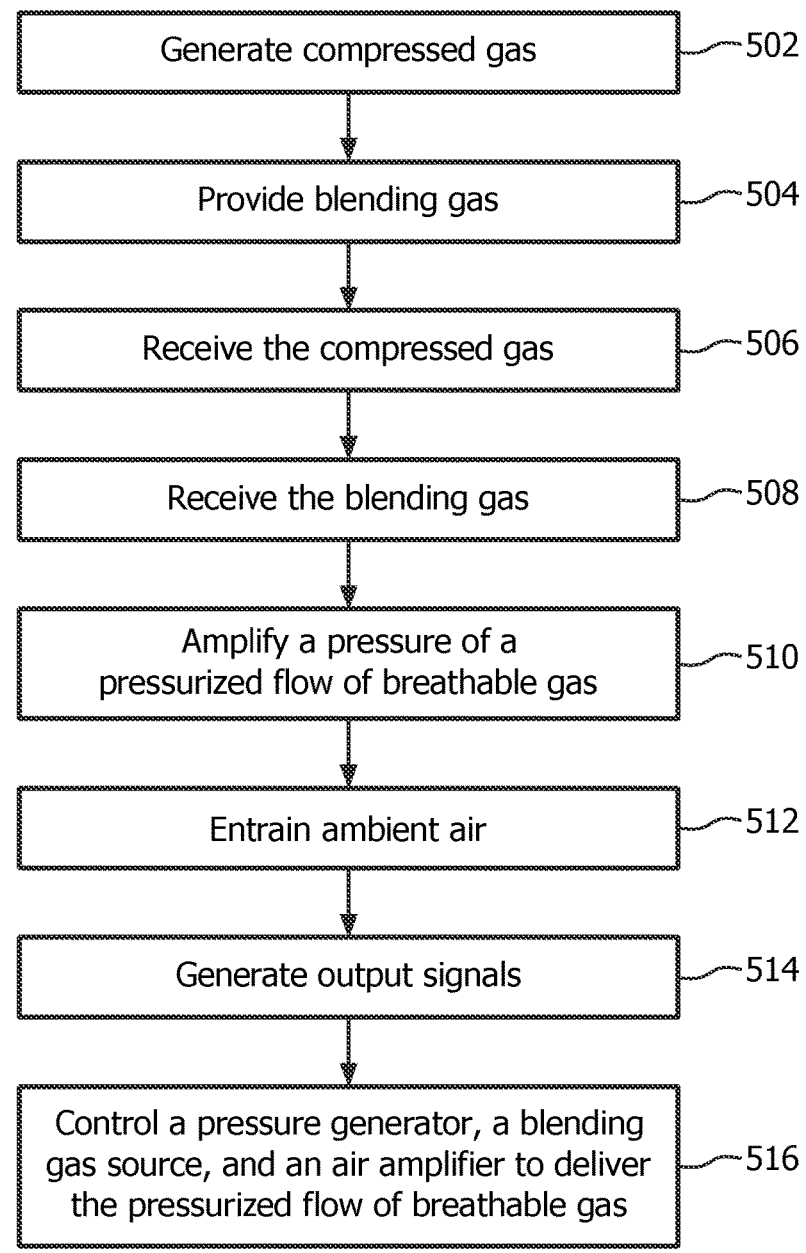
FIG. 5 illustrates a method for delivering a blending gas enriched pressurized flow of breathable gas to the airway of a subject with a ventilation system.

FIG. 5 illustrates a method 500 for delivering a blending gas enriched pressurized flow of breathable gas to the airway of a subject with a delivery system. The system comprises a pressure generator, a blending gas source, an air amplifier, a venturi valve, one or more sensors, one or more physical computer processors, and/or other components. The operations of method 500 presented below are intended to be illustrative. In some embodiments, method 500 may be accomplished with one or more additional operations not described, and/or without one or more of the operations discussed. Additionally, the order in which the operations of method 500 are illustrated in FIG. 5 and described below is not intended to be limiting.

In some embodiments, method 500 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 500 in response to instructions stored electronically on an electronic storage medium. The one or more processing devices may include one or more devices configured through hardware, firmware, and/or software to be specifically designed for execution of one or more of the operations of method 500.

At an operation 502, compressed gas is generated. In some embodiments, operation 502 is performed by a pressure generator the same as or similar to pressure generator 14 (shown in FIG. 1 and described herein).

At an operation 504, blending gas is provided. In some embodiments, the blending gas is oxygen and/or other blending gases. In some embodiments, the blending gas source is an oxygen concentrator, bottled compressed oxygen, liquid oxygen, and/or another blending gas source. In some embodiments, operation 504 is performed by a blending gas source the same as or similar to blending gas source 25 (shown in FIG. 1 and described herein).

At an operation 506, the compressed gas is received. The compressed gas is received from the pressure generator by the air amplifier. In some embodiments, operation 506 is performed by an air amplifier the same as or similar to air amplifier 40 (shown in FIG. 1 and described herein).

At an operation 508, the blending gas is received. The blending gas is received from the blending gas source into the pressurized flow of breathable gas. In some embodiments, operation 508 is performed by an air amplifier the same as or similar to air amplifier 40 (shown in FIG. 1 and described herein).

At an operation 510, a pressure of the pressurized flow of breathable gas is amplified. The amplified pressurized flow of breathable gas includes the blending gas. In some embodiments, operation 510 is performed by an air amplifier the same as or similar to air amplifier 40 (shown in FIG. 1 and described herein).

At an operation 512, ambient air is entrained with the venturi valve. The venturi valve receives the pressurized flow of breathable gas from the air amplifier and then entrains the ambient air into the pressurized flow of breathable gas. The venturi valve entrains the ambient air during inhalation of the subject. In some embodiments, operation 512 is performed by a venturi valve the same as or similar to venturi valve 50 (shown in FIG. 1 and described herein).

At an operation 514, output signals are generated. The output signals convey information related to one or more gas parameters of the pressurized flow of breathable gas. In some embodiments, operation 514 is performed by a one or more sensors the same as or similar to sensors 18 (shown in FIG. 1 and described herein).

At an operation 516, the pressure generator, the blending gas source, and the air amplifier are controlled to deliver the pressurized flow of breathable gas to the subject. The pressure generator, the blending gas source, and the air amplifier are controlled to deliver the pressurized flow of breathable gas in accordance with a bi-level positive pressure support therapy regime. The pressure generator, the blending gas source, and the air amplifier are controlled to deliver the pressurized flow of breathable gas based on the output signals from sensors 18. In some embodiments, controlling the pressure generator, the blending gas source, and the air amplifier to deliver the pressurized flow of breathable gas to the subject according to a bi-level positive pressure support therapy regime includes determining inhalation phases and/or exhalation phases during breathing of the subject based on the output signals; controlling the pressure generator to adjust a positive end expiratory pressure in the subject based on the output signals, the inhalation and/or exhalation phase determinations, and the bi-level pressure support therapy regime; and controlling the blending gas source to adjust an amount of blending gas in the pressurized flow of breathable gas based on the output signals, the inhalation and/or exhalation phase determinations, and the bi-level pressure support therapy regime. In some embodiments, operation 516 is performed by one or more physical computer processors the same as or similar to physical computer processors 20 (shown in FIG. 1 and described herein).

In some embodiments, the system further comprises a subject interface including a conduit and an interface appliance. In some embodiments, the method further comprises operations including communicating, with the subject interface, the pressurized flow of breathable gas from the venturi valve to the airway of the subject; coupling the pressure generator, the blending gas source, the air amplifier, and the venturi valve with the interface appliance via the conduit; and locating the pressure generator, the blending gas source, the air amplifier, and the venturi valve remotely from the interface appliance to reduce noise from the pressure generator, the blending gas source, the air amplifier, and/or the venturi valve heard by the subject.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

The invention claimed is:

1. A system configured to deliver a blending gas enriched pressurized flow of breathable gas to the airway of a subject, the system comprising:
  a pressure generator configured to generate compressed gas;
  a blending gas source configured to provide blending gas;
  an air amplifier configured to receive the compressed gas from the pressure generator and the blending gas from the blending gas source into the pressurized flow of breathable gas, and amplify a pressure of the pressurized flow of breathable gas that includes the blending gas;
  a venturi valve configured to receive the pressurized flow of breathable gas from the air amplifier and entrain ambient air into the pressurized flow of breathable gas during inhalation of the subject;
  an interface appliance coupled to, and in direct communication with, the venturi valve by a flexible conduit, the interface appliance being configured to communicate the pressurized flow of breathable gas communicated from the venturi valve via the conduit to the airway of the subject;
  one or more sensors configured to generate output signals conveying information related to one or more gas parameters of the pressurized flow of breathable gas; and
  one or more physical computer processors configured by computer readable instructions to control the pressure generator, the blending gas source, and the air amplifier to deliver the pressurized flow of breathable gas to the subject according to a bi-level positive pressure support therapy regime based on the output signals,
  wherein the pressure generator, the blending gas source, the air amplifier, and the venturi valve are provided in a grouping located remotely from the interface appliance to reduce noise from the pressure generator, the blending gas source, the air amplifier, and/or the venturi valve heard by the subject.

2. The system of claim 1, wherein the blending gas source is configured such that the blending gas is oxygen, and wherein the blending gas source is an oxygen concentrator, bottled compressed oxygen, or liquid oxygen.

3. The system of claim 1, wherein the one or more physical computer processors are configured such that controlling the pressure generator, the blending gas source, and the air amplifier to deliver the pressurized flow of breathable gas to the subject according to the bi-level positive pressure support therapy regime includes:
  determining inhalation phases and/or exhalation phases during breathing of the subject based on the output signals;
  controlling the pressure generator to adjust a positive end expiratory pressure in the subject based on the output signals, the inhalation and/or exhalation phase determinations, and the bi-level pressure support therapy regime; and
  controlling the blending gas source to adjust an amount of the blending gas in the pressurized flow of breathable gas based on the output signals, the inhalation and/or exhalation phase determinations, and the bi-level pressure support therapy regime.

4. The system of claim 1, wherein the grouping is positioned within a portable bag while the blending gas enriched pressurized flow of breathable gas is delivered to the airway of the subject.

5. The system of claim 4, wherein the portable bag is structured to be carried on the subject while the blending gas enriched pressurized flow of breathable gas is delivered to the airway of the subject.

6. The system of claim 4 wherein the portable bag is structured to be carried on the subject about the hips of the subject while the blending gas enriched pressurized flow of breathable gas is delivered to the airway of the subject.

7. The system of claim 1, wherein the interface appliance comprises one of: a nasal cannula, a nasal mask, a nasal/oral mask, a full face mask, or a total face mask.

8. A method for delivering a blending gas enriched pressurized flow of breathable gas with a delivery system, the system comprising: a pressure generator, a blending gas source, an air amplifier, one or more sensors, one or more physical computer processors, a venturi valve, a flexible conduit, and an interface appliance configured to communicate the pressurized flow of breathable gas to the airway of the subject, the method comprising:
  locating the pressure generator, the blending gas source, the air amplifier, and the venturi valve in a grouping remote from the interface appliance to reduce noise from the pressure generator, the blending gas source, the air amplifier, and/or the venturi valve heard by the subject;

coupling the pressure generator, the blending gas source, the air amplifier, and the venturi valve with the interface appliance via the flexible conduit, with the venturi valve being in direct communication with the interface appliance;

generating compressed gas with the pressure generator;

providing blending gas with the blending gas source;

receiving the compressed gas from the pressure generator with the air amplifier;

receiving the blending gas from the blending gas source with the air amplifier;

amplifying a pressure of the pressurized flow of breathable gas that includes the blending gas with the air amplifier;

receiving, with the venturi valve, the pressurized flow of breathable gas from the air amplifier and entraining ambient air into the pressurized flow of breathable gas during inhalation of the subject;

generating, with the one or more sensors, output signals conveying information related to one or more gas parameters of the pressurized flow of breathable gas; and controlling, with the one or more physical computer processors, the pressure generator, the blending gas source, and the air amplifier to deliver the pressurized flow of breathable gas to the subject according to a bi-level positive pressure support therapy regime based on the output signals.

9. The method of claim 8, wherein the blending gas is oxygen, and wherein the blending gas source is an oxygen concentrator, bottled compressed oxygen, or liquid oxygen.

10. The method of claim 8, wherein controlling the pressure generator, the blending gas source, and the air amplifier to deliver the pressurized flow of breathable gas to the subject according to the bi-level positive pressure support therapy regime includes:

determining inhalation phases and/or exhalation phases during breathing of the subject based on the output signals;

controlling the pressure generator to adjust a positive end expiratory pressure in the subject based on the output signals, the inhalation and/or exhalation phase determinations, and the bi-level pressure support therapy regime; and controlling the blending gas source to adjust an amount of the blending gas in the pressurized flow of breathable gas based on the output signals, the inhalation and/or exhalation phase determinations, and the bi-level pressure support therapy regime.

11. The method of claim 8, wherein the grouping is positioned within a portable bag while the pressurized flow of breathable gas is delivered to the subject.

* * * * *